US009017306B2

(12) United States Patent
Carbonari et al.

(10) Patent No.: US 9,017,306 B2
(45) Date of Patent: Apr. 28, 2015

(54) DISPOSABLE ABSORBENT PRODUCT WITH FASTENING COMPONENTS AND RELATED METHODS

(75) Inventors: Raquel Carbonari, Philadelphia, PA (US); Mariela Biber, Ardmore, PA (US)

(73) Assignee: SCA Hygiene Products AB, Gothenburg (SE)

( * ) Notice: Subject to any disclaimer, the term of this patent is extended or adjusted under 35 U.S.C. 154(b) by 593 days.

(21) Appl. No.: 13/334,832

(22) Filed: Dec. 22, 2011

(65) Prior Publication Data

US 2013/0165897 A1    Jun. 27, 2013

(51) Int. Cl.
*A61F 13/15*    (2006.01)
*A61F 13/56*    (2006.01)

(52) U.S. Cl.
CPC ....... *A61F 13/5622* (2013.01); *A61F 13/15723* (2013.01); *A61F 13/15756* (2013.01)

(58) Field of Classification Search
CPC ........... A61F 13/5622; A61F 13/15577; A61F 13/15723; A61F 13/56; A61F 2013/49087; A44B 99/00
USPC .................. 604/383, 385.01, 385.09, 385.11, 604/385.14, 386–393
See application file for complete search history.

(56) References Cited

U.S. PATENT DOCUMENTS 4,211,226 A * 7/1980 Schaar ........................... 604/370
4,909,802 A * 3/1990 Ahr et al. .................... 604/385.3
5,422,172 A   6/1995 Wu
5,797,896 A   8/1998 Schmitz
6,110,157 A * 8/2000 Schmidt .................... 604/385.01

(Continued)

FOREIGN PATENT DOCUMENTS

EP      2266512 A1   12/2010
EP      2266516 A1   12/2010
WO   WO-0226183 A1    4/2002

OTHER PUBLICATIONS

International Search Report and Written Opinion mailed Jan. 31, 2013, issued in International Patent Application No. PCT/EP2012/074630, filed Dec. 6, 2012.

(Continued)

*Primary Examiner* — Michele M Kidwell
(74) *Attorney, Agent, or Firm* — Drinker Biddle & Reath LLP

(57) ABSTRACT

A disposable absorbent product extends along a longitudinal axis between front and back longitudinal ends of the product, and along a transverse axis. The product has a topsheet defining an interior face of the product configured to face a wearer thereof during use, and a backsheet overlaying the topsheet, the backsheet defining an exterior face of the product. An absorbent core is disposed between the topsheet and the backsheet for storing fluid secreted by the wearer of the product. The product also includes a first pair of fastening components, each being formed from a partially cut-out portion of the disposable absorbent product so as to be pivotally coupled to a remainder of the product, such that pivotal movement of the fastening components relative to a remainder of the product defines at least one aperture that extends between the interior and exterior faces of the product.

19 Claims, 6 Drawing Sheets

(56) References Cited

U.S. PATENT DOCUMENTS

| | | |
|---|---|---|
| 6,544,375 B1 | 4/2003 | Schmitz |
| 6,638,261 B2 * | 10/2003 | Suzuki .................... 604/385.13 |
| 6,730,070 B2 * | 5/2004 | Holmquist ................... 604/392 |
| 7,641,641 B2 * | 1/2010 | Ramshak ................ 604/385.01 |
| 7,849,536 B2 * | 12/2010 | Lindstrom ........................ 5/484 |
| 8,246,594 B2 * | 8/2012 | Sperl et al. .............. 604/385.16 |
| 2006/0216473 A1 | 9/2006 | Tomany et al. |
| 2006/0241559 A1 * | 10/2006 | Buhrow et al. .......... 604/385.09 |
| 2007/0250032 A1 | 10/2007 | Andrews |
| 2009/0036860 A1 | 2/2009 | Sugiyama et al. |

OTHER PUBLICATIONS

International Preliminary Report on Patentability dated Jun. 24, 2014, issued in International Patent Application No. PCT/EP2012/074630, filed Dec. 6, 2012.

* cited by examiner

DISPOSABLE ABSORBENT PRODUCT WITH FASTENING COMPONENTS AND RELATED METHODS

TECHNICAL FIELD

The present invention is generally related to absorbent products and, more particularly, to disposable absorbent products that are worn by humans for the containment and absorption of fluid bodily secretions.

BACKGROUND

Disposable absorbent products for absorption of bodily fluids are available in different types, designs, and dimensions. For example, training pants, baby diapers, adult diapers, and incontinence guards are products designed for the containment of urine and excrement. There are other types of disposable absorbent articles, such as feminine hygiene products (e.g., heavy and light incontinence pads, pantiliners) that are designed to contain and absorb urine and/or menses secreted by female wearers. Known products of this type typically include a topsheet facing the body of the wearer, a backsheet facing the garment worn by the wearer, and an absorbent core sandwiched between the topsheet and backsheet.

In conventional disposable absorbent products, such as diapers, the range of body shapes about which those diapers may fit is determined by the overall lateral extent i.e., the width of the diapers. In this regard, diaper manufacturers that wish for their products to fit around relatively large wearers' bodies conventionally design relatively wide diapers. But the manufacture of relatively wide diapers adds to the amount of material required to be used, which makes the overall manufacturing cost of those diapers relatively high. Further, the manufacture of relatively wide diapers requires equipment specifically configured for that purpose, which makes the overall manufacturing costs high.

In conventional diapers also, the types of materials used in their manufacture sometimes causes the accumulation of heat and moisture in the areas of the wearer's body that are covered by those diapers. To address this concern, diapers have been known to include "breathable" materials, which permit the flow of air between the interior and exterior of the diaper during use. But these "breathable" materials can be expensive and/or complex to handle in a manufacturing setting.

Accordingly, it is desirable to provide disposable absorbent products that address these and other shortcomings of conventional disposable absorbent products.

SUMMARY

In one embodiment, a disposable absorbent product is provided that extends along a longitudinal axis between front and back longitudinal ends of the disposable absorbent product, and along a transverse axis orthogonal to the longitudinal axis. The disposable absorbent product has a topsheet defining an interior face of the disposable absorbent product configured to face a wearer thereof during use, and a backsheet overlaying the topsheet, the backsheet defining an exterior face of the disposable absorbent product configured to face away from the wearer during use. An absorbent core is disposed between the topsheet and the backsheet for storing fluid secreted by the wearer of the disposable absorbent product.

The product also includes a first pair of fastening components, each being formed from a partially cut-out portion of the disposable absorbent product so as to be pivotally coupled to a remainder of the disposable absorbent product, such that pivotal movement of the fastening components relative to a remainder of the disposable absorbent product defines at least one aperture that extends between the interior and exterior faces of the disposable absorbent product.

In specific embodiments, pivotal movement of the fastening components relative to the remainder of the disposable absorbent product defines a pair of laterally spaced apart apertures that extend between the interior and exterior faces of the disposable absorbent product. In other specific embodiments the absorbent core has first and second longitudinal edges, and the absorbent core is longitudinally positioned in the disposable absorbent product so as to leave first and second end portions respectively between the first longitudinal edge and one of the front or back longitudinal ends, and between the second longitudinal edge and the other of the front or back longitudinal ends. In those other specific embodiments, each of the fastening components is formed from a partially cut-out portion in the first end portion, with each of the fastening components being pivotally coupled to the first end portion. In those embodiments also, pivotal movement of each of the fastening components relative to the first end portion defines the at least one aperture, with the at least one aperture being located in the first end portion.

Additionally, the first longitudinal edge of the absorbent core may be proximate the back longitudinal end, with the first end portion extending between the first longitudinal edge and the back longitudinal end, and with the fastening components being located in the first end portion. Each of the fastening components may include a mechanical fastening element. Additionally or alternatively, each of the fastening components may include an interior face that is coplanar with the interior face of the disposable absorbent product, and an exterior face that is coplanar with the exterior face of the disposable absorbent product, with a fastening element being coupled to the interior face of the fastening component.

In particular embodiments, at least a portion of each of the fastening components is activated. In those embodiments, the portion that is activated may have a layer of elastomeric material therein. In other embodiments, a layer of elastomeric material is disposed between the topsheet and backsheet, with the fastening components including that elastomeric material, and with at least a portion of each of the fastening components that contains the elastomeric material being activated. Additionally, in those embodiments, areas of the disposable absorbent product that contain the elastomeric material and that are adjacent the fastening components may be free of activation.

In other specific embodiments, the transverse axis conceptually divides the disposable absorbent product into front and back longitudinal halves, and the disposable absorbent product also has a second pair of fastening components located on the front or back longitudinal half and which are engageable with a cooperating fastening feature on the other of the front or back longitudinal halves so as to secure the disposable absorbent product in place during use. The fastening feature may be a component attached to the backsheet, or may alternatively be defined by an exterior surface of the backsheet.

The disposable absorbent product may additionally have a fastening feature attached to the backsheet and that is engageable by at least one of the fastening components to secure the disposable absorbent product in place during use. In particular embodiments, each of the fastening components is joined to a remainder of the disposable absorbent product through a frangible joint. Additionally, in those embodiments, each of the fastening components may be further joined to the remainder of the disposable absorbent product through a solid joint.

In another embodiment, a disposable absorbent product is provided that extends in a longitudinal dimension between front and back longitudinal ends of the product, and in a width dimension orthogonal to the longitudinal dimension. The disposable absorbent product has a topsheet defining an interior face of the disposable absorbent product configured to face a wearer thereof during use, and a backsheet overlaying the topsheet, with the backsheet defining an exterior face of the disposable absorbent product configured to face away from the wearer during use. An absorbent core is disposed between the topsheet and the backsheet for storing fluid secreted by the wearer of the disposable absorbent product.

The product also has a pair of fastening components, each having an interior face and an exterior face disposed opposite the interior face of the fastening component, with each fastening component having a first condition in which the exterior face thereof is coplanar with the exterior face of the disposable absorbent product, and a second condition in which the exterior face of the fastening component is not coplanar with the exterior face of the disposable absorbent product. Movement of the fastening components between the first and second conditions defines at least one aperture adjacent at least one of the fastening components and which extends between the interior and exterior faces of the disposable absorbent product.

In specific embodiments, the disposable absorbent product also has a frangible joint between each of the fastening components and a remainder of the disposable absorbent product, such that movement of the fastening components from the first condition to the second condition includes rupturing of the frangible joint. Additionally, the product may also have a solid joint between each of the fastening components and the remainder of the disposable absorbent product, with the solid joint coupling the fastening component to the remainder of the disposable absorbent product in the first and second conditions.

Yet in another embodiment, a method is provided for forming a disposable absorbent product that includes a topsheet and a backsheet overlaying one another, and an absorbent core that is disposed between the topsheet and backsheet. The method includes coupling a pair of fastening elements to the disposable absorbent product, and partially cutting a pair of portions of the disposable absorbent product containing the fastening elements so as to define a pair of fastening components that are pivotally coupled to a remainder of the disposable absorbent product.

The method may be such that partially cutting the pair of portions includes forming a frangible joint between each of those portions and the remainder of the disposable absorbent product. Additionally, the method may be such that partially cutting the pair of portions includes forming a solid joint between each of those portions and the remainder of the disposable absorbent product. In specific embodiments, the portions include a layer of elastomeric material therein, and the method includes activating the pair of portions. Additionally, activating those portions may include activating those portions while leaving adjacent areas of the disposable absorbent product containing the layer of elastomeric material therein unactivated.

BRIEF DESCRIPTION OF THE DRAWINGS

The objectives and features of the invention will become more readily apparent from the following detailed description taken in conjunction with the accompanying drawings in which.

DETAILED DESCRIPTION

Figure 1:
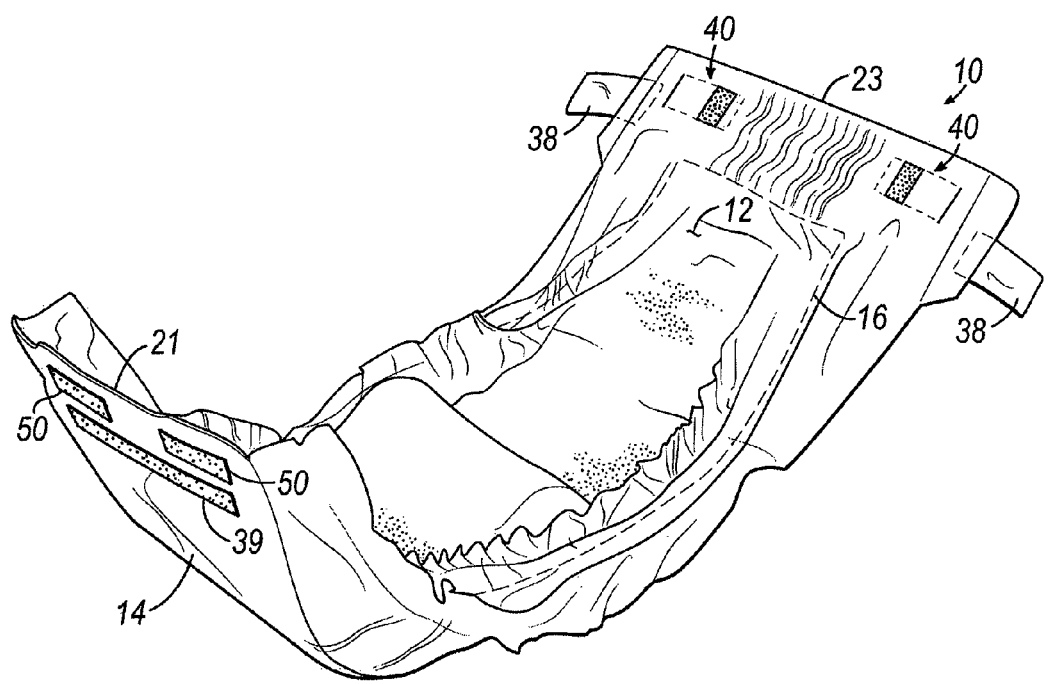
FIG. 1 is a perspective view of a disposable absorbent product in accordance with one embodiment of the invention.
Figure 2:
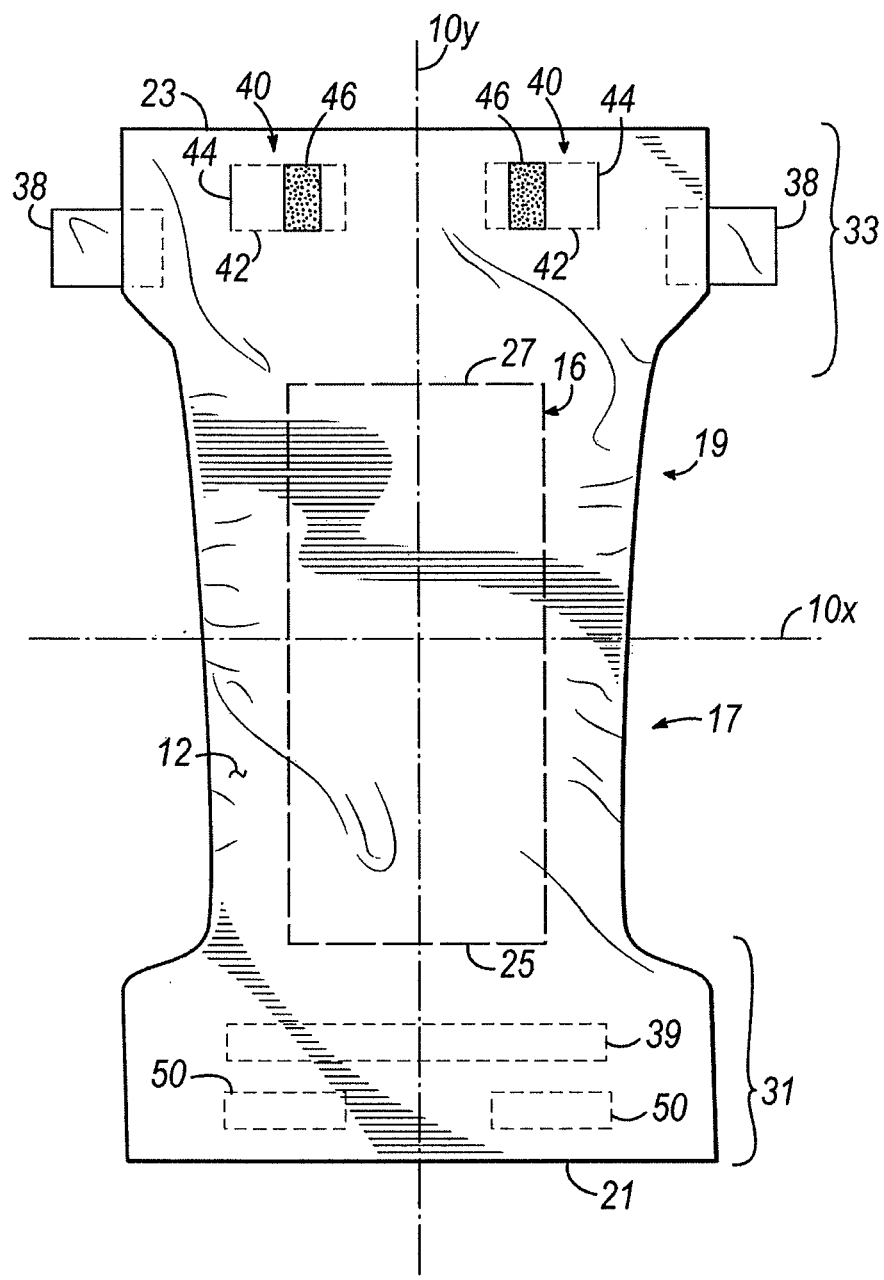
FIG. 2 is a top view of the disposable absorbent product of FIG. 1.

With reference to the figures, and more particularly to FIGS. 1 and 2, an exemplary disposable absorbent product in the form of a diaper 10 is illustrated. Diaper 10 could be a baby diaper or an adult diaper ("brief") or a belted undergarment, for example. While these and other figures refer to a disposable absorbent product in the form of a diaper, it is contemplated that one or more of the features described and/or illustrated herein are applicable to other types of disposable absorbent products, and these are therefore not limited to the exemplary diapers described herein. For example, and without limitation, one or more of the various features described herein may be also used in training pants, adult-size disposable pads, feminine catamenial pads, or male or female light-incontinence, medium-incontinence, or heavy-incontinence pads.

The exemplary diaper 10 includes a topsheet 12 and a backsheet 14 disposed opposite the topsheet 12, such that the topsheet 12 and backsheet 14 are in an overlaying relationship with one another. In use, the topsheet 12 at least partially defines an interior face IF of the diaper 10 that faces the body of the wearer. The backsheet 14, by contrast, faces away from the body of the wearer and at least partially defines an exterior face EF of the diaper 10. The topsheet 12 is made of a permeable, hydrophilic material such as a hydrophilic nonwoven, and may be in the form of a single, continuous layer across the length and width of the diaper 10, or may alternatively be in the form of two or more layers of the same material or of materials different from one another that jointly, rather than individually, span the length and width of the diaper 10.

The backsheet 14 is made of an impermeable, hydrophobic material such as a hydrophobic nonwoven or a laminate made of one or more layers of nonwoven material and one or more layers of polypropylene or polyethylene film. Backsheet 14 may be in the form of a single, continuous layer across the length and width of the diaper 10, or may alternatively be in the form of two or more layers of the same material or of materials different from one another that jointly, rather than individually, span the length and width of the diaper 10.

The pad 10 also includes an absorbent core 16, disposed between the topsheet 12 and backsheet 14, which is configured to absorb and retain body fluids, such as urine and/or menses, secreted by the wearer. The core 16 is made up of fluff pulp or a combination of fluff pulp or some other natural or synthetic fluid management material, and a fluid storage material such as superabsorbent material ("SAP") or some other natural or synthetic fluid storage material. While not shown, core 16 may also include an optional acquisition material layer or another type of layer (e.g., an airlaid material layer) adjacent the topsheet 12, which is primarily configured to distribute and/or direct fluids received through the topsheet 12 onto other portions of core 16 that are primarily configured to store fluids secreted by the wearer. The core 16 could be generally rectangular, or have an hourglass shape, or have any other regular or irregular, symmetrical or asymmetrical shape.

With continued reference to FIGS. 1-2, the core 16 and the pad 10 of which core 16 forms part, extend along a longitudinal axis 10y (longitudinal dimension), and along a transverse axis 10x (width dimension) orthogonal to the longitudinal axis 10y. The transverse axis 10x, in this embodiment, conceptually divides the diaper 10 into front and back longitudinal halves 17, 19. The diaper 10 thus extends longitudinally between a front longitudinal end 21 and a back longitudinal end 23. The core 16, in turn, extends longitudinally between a front edge 25 and a back edge 27. While the front and back edges 25, 27 are illustrated in the figures as generally rectilinear, it is understood either or both may have any other regular or irregular shape, such as one including curves, straight line segments or any other shape. In use, the diaper 10 is oriented such that the front longitudinal end 21 and the front edge 25 are proximate the front part of the body of the wearer, and such that the back longitudinal end 23 and the back edge 27 are proximate the back part of the wearer's body.

The core 16 of the illustrated embodiment is positioned relative to other portions of the diaper 10, such that a front end portion 31 is defined between the front longitudinal end 21 and the front edge 25 of the core 16. The exemplary core 16 is also positioned so as to define a back end portion 33 between the back longitudinal end 23 and the back edge 27 of the core 16. Those of ordinary skill in the art will readily appreciate, however, that other relative positions of the core 16 are possible which may, for example, define only one end portion 31, 33 or define no such end portions at all. In other words, alternative configurations are contemplated in which the core 16 may instead extend to one or both of the longitudinal ends 21, 23. In addition, the front and back end portions 31, 33 in the illustrated embodiment are substantially free of the materials making up core 16 i.e., free of materials of core 16 that generally give core 16 its shape. In that regard, embodiments are contemplated in which one or both of the front or back end portions 31, 33 may have some relatively small amounts of core material e.g., SAP, and still be considered to be "substantially free" of materials making up core 16.

With continued reference to FIGS. 1-2, diaper 10 includes a pair of fastening components such as mechanical fasteners or adhesive or cohesive tapes, generally assigned the numeral 38, located in the back longitudinal half 19 of diaper 10, adjacent the lateral ends LE of the diaper 10. The fastening components 38 are engageable with a cooperating fastening feature 39 on the front longitudinal half 17 of the diaper 10 to secure the diaper 10 in place, on the body of the wearer. The cooperating fastening feature 39 may for example be in the form of an adhesive or cohesive landing zone or patch, or a mechanical fastener landing zone or patch (e.g., containing hooks or loops) coupled (e.g., mechanically and/or adhesively attached) to the backsheet 14 and which cooperates with fastening component 38 to secure the diaper 10 in place, on the body of the wearer.

Fastening feature 39 may alternatively be defined by the exterior surface of the backsheet 14, so long as that surface is configured to engage the fastening component 38 sufficiently so as to secure the diaper 10 in place i.e., on the body of the wearer. While the embodiment of FIGS. 1-2 has the fastening components 38 located in the back longitudinal half 19 and the cooperating fastening feature 39 being located in the front longitudinal half 17, embodiments are contemplated in which the fastening components 38 are instead located in the front longitudinal half 17, while the cooperating fastening feature 39 is located in the back longitudinal half 19, so long as they are positioned so as to engage one another to secure the diaper 10 in place. Yet other embodiments are contemplated that include no fastening components or cooperating fastening features of the type exemplified by the fastening components 38 and fastening feature 39 of this embodiment.

Figure 3:
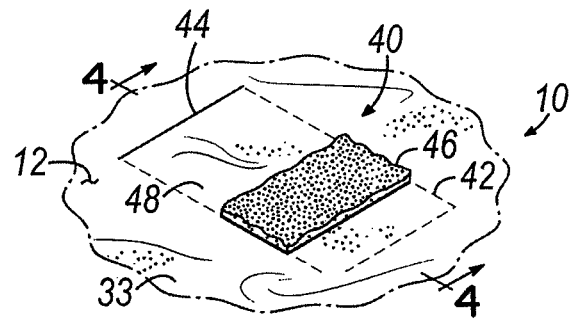
FIG. 3 is perspective broken-away view of a portion of the disposable absorbent product of FIGS. 1-2, showing a fastening component thereof in a first condition.
Figure 4:
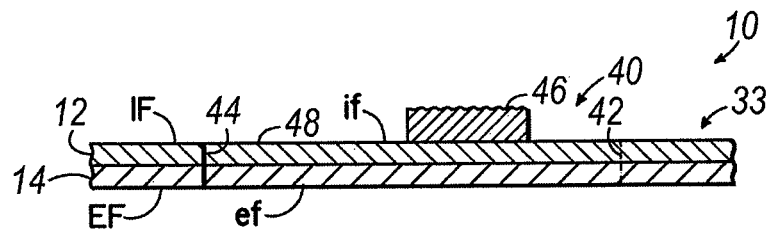
FIG. 4 is a schematic cross-sectional view taken along line 4-4 of FIG. 3.

With continued reference to FIGS. 1-2, and further referring to FIGS. 3 and 4, diaper 10 has an additional pair of fastening components 40 that are formed from partially cut-out portions of the back end portion 33, in the back longitudinal half 19. The fastening components 40 in the embodiment of FIG. 3 are in the form of generally-rectangular tabs, each of which is partially joined to the remainder of back end portion 33. More specifically, each fastening component 40 in the illustrated embodiment is joined to adjacent sections of the back end portion 33 through a generally C-shaped frangible joint 42 and a solid joint 44. The shapes, dimensions, and orientations of the frangible and solid joints 42, 44 are merely exemplary and thus not intended to be limiting.

A fastening element 46, which may be an adhesive layer, cohesive layer, or mechanical fastening element (e.g., containing hooks or loops), is coupled to a main body 48 of the fastening component 40 and is engageable with a cooperating fastening feature 50 (FIG. 1), located in the front longitudinal half 17. The cooperating fastening feature 50 may be in the form of an adhesive or cohesive landing zone or patch, or a mechanical fastener landing zone or patch (e.g., containing hooks or loops) coupled (e.g., mechanically and/or adhesively attached) to the backsheet 14 and which cooperates with fastening element 46 of fastening component 40 to secure the diaper 10 in place, on the body of the wearer. Fastening feature 50 may alternatively be defined by the exterior surface of the backsheet 14, so long as that surface is configured to engage the fastening element 46 sufficiently to secure the diaper 10 in place i.e., on the body of the wearer.

An alternative embodiment is contemplated in which the diaper 10 has two pairs of fastening components 38, 40, and a single fastening feature such as fastening feature 39 or fastening feature 50. In that embodiment, the wearer or otherwise user of the diaper may choose to engage either pair of the fastening components 38, 40 with that single fastening feature (e.g., 39 or 50) to secure the diaper on the body of the wearer.

The fastening element 46 is in certain embodiments a layer of material that has an adhesive backing, with the adhesive backing being designed to engage the topsheet 12 or backsheet 14 at the back end portion 33 so as to become integral therewith. In that regard, material making up the fastening element 46 may, for example, be delivered in the form of a continuous web, which is then cut and applied onto the back end portion 33 through a cut-and-slip process, for example. An exemplary cut-and-slip process is described in U.S. Pat. No. 6,544,375, entitled "PROCESS FOR APPLYING DISCRETE WEB PORTIONS TO A RECEIVING WEB," the entire contents of which are hereby incorporated by reference herein. A die-cutting roll having discrete cutting edges and continuous cutting edges can then be used to partially cut the back end portion 33 so as to respectively generate the frangible joint 42 and solid joint 44. These processes are exemplary, insofar as other high-speed, low-speed, automatic or manual processes are contemplated to form the fastening components 40.

Figure 5:
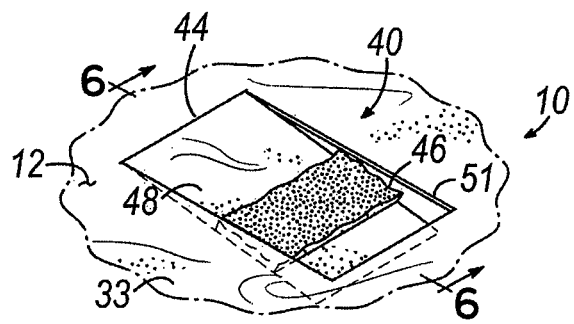
FIG. 5 is a perspective broken-away view, similar to FIG. 3, showing the fastening component in a second condition.
Figure 6:
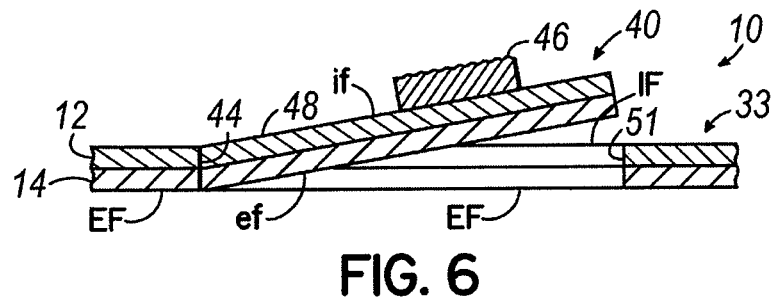
FIG. 6 is a schematic cross-sectional view, similar to FIG. 4, taken along line 6-6 of FIG. 5.

With continued reference to FIGS. 1-4, and further referring now to FIGS. 5 and 6, each of the fastening components 40 has a first condition and a second condition. In the first condition, illustrated at FIGS. 3 and 4, the exemplary fastening component 40 shown therein is coplanar with the back end portion 33 from which it is formed. More specifically, in that condition, an exterior face "ef" of the fastening component 40 is coplanar with surrounding portions of the exterior face EF of the diaper 10. In that condition also, an interior face "if" of the fastening component 40 is coplanar with surrounding portions of the interior face IF of diaper 10. In this embodiment, the fastening elements 46 are located on the respective interior faces "if" of the fastening components 40, although it is contemplated that they may instead be located on the exterior faces "ef" of the fastening components 40.

In the first condition of the fastening component 40 shown in FIGS. 3 and 4, the frangible joint 42 is not ruptured but rather joins the fastening component 40 with adjacent areas of the back end portion 33. The illustrated first condition of fastening component 40 may be, in some embodiments, associated with the condition of the diaper 10 in a commercially-available package containing same. Alternative embodiments are contemplated in which there are no frangible joints 42 at all, but rather in which a portion of the fastening component 40 is not coupled at all to the surrounding areas of back end portion 33.

FIGS. 5 and 6 illustrate a second condition of fastening component 40, resulting from pivotal movement of fastening component 40, about the pivotal coupling provided by solid joint 44, relative to remaining portions of the back end portion 33. In this exemplary second condition, the frangible joint 42 has been ruptured to allow relative movement of the fastening component 40, such that neither of the interior or exterior faces "if, ef" of fastening component 40 is respectively coplanar with the interior and exterior faces IF, EF of diaper 10. Movement of the fastening components 40 away from the first condition (FIGS. 3 and 4) defines a pair of laterally spaced apart apertures 51 of diaper 10 (only one of the apertures 51 is shown in FIG. 5) that extend through the entire thickness of back end portion 33 i.e., between the interior and exterior faces IF, EF of diaper 10. The apertures 51 provide ventilation to the body of the wearer during use. The second condition of fastening component 40 may be associated, in some embodiments, with the condition of the diaper 10 during use. More specifically, movement of the fastening component 40 away from the first condition (FIGS. 3 and 4) permits the user of the diaper 10, such as the wearer or a caretaker thereof, to engage the fastening element 46 of fastening component 40 with the cooperating fastening feature 50 on the front longitudinal half of diaper 10 (FIGS. 1 and 2).

Figure 7:
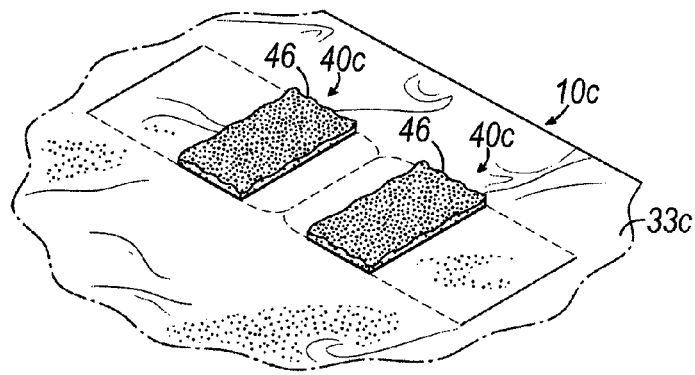
FIG. 7 is a top view of a pair fastening components in accordance with another embodiment of the invention.
Figure 7A:
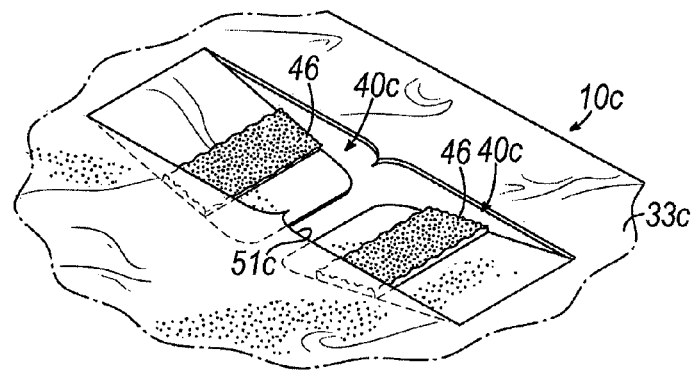
FIG. 7A is a perspective view of the fastening components of FIG. 7.

A variation, shown in FIGS. 7 and 7A, is contemplated in which the fastening components 40c therein are located in a back end portion 33c of an exemplary diaper 10c so as to be in an abutting relationship with one another in the first condition (FIGS. 3 and 4). In that alternative embodiment, movement of the fastening components 40c away from the first condition defines a single aperture 51c that also provides ventilation to the wearer of the diaper 10. For ease of understanding, like reference numerals in FIGS. 7 and 7A refer to similar features in the preceding figures.

Figure 8:
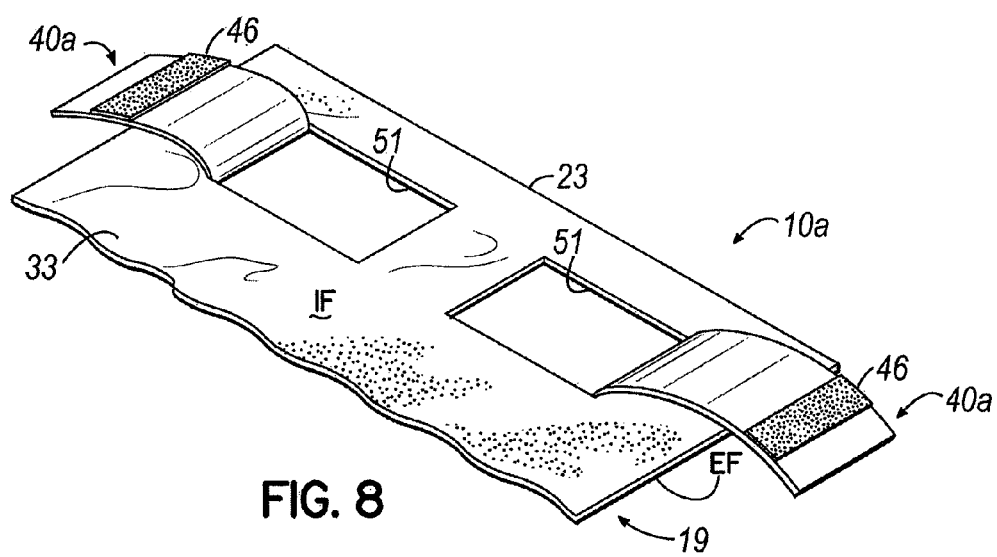
FIG. 8 is a perspective broken-away view of a disposable absorbent product with fastening components in accordance with another embodiment of the invention.
Figure 9:
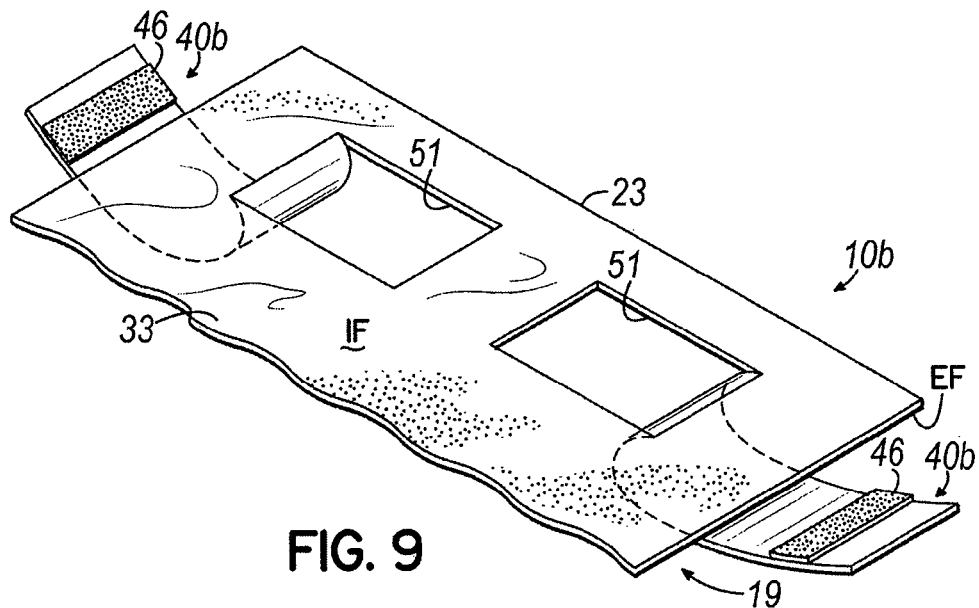
FIG. 9 is a perspective broken-away view of a disposable absorbent product with fastening components in accordance with yet another embodiment of the invention.

FIGS. 8 and 9 illustrate exemplary movements of fastening components 40a, 40b relative to other portions of respective diapers 10a, 10b. In those figures, like reference numerals refer to similar features in the preceding figures. FIG. 8 shows movement of fastening components 40a in a direction toward the interior face IF of diaper 10a, while FIG. 9 shows movement of the fastening components 40b therein in a direction toward the exterior face EF, and away from interior face IF, of diaper 10. FIGS. 8 and 9 both illustrate the increased extension of diaper 10a, 10b provided by the fastening components 40a, 40b. More specifically, the fastening components 40a, 40b (and fastening components 40 and 40c of the other figures herein) provide increased lateral extension of the back longitudinal half 19 of diaper 10, 10a, 10b, 10c. This increased lateral extension of diaper 10, 10a, 10b, 10c may facilitate application and fit of diaper 10, 10a, 10b, 10c around wearers' bodies larger than possible without fastening components 40, 40a, 40b, 40c.

Figure 10:
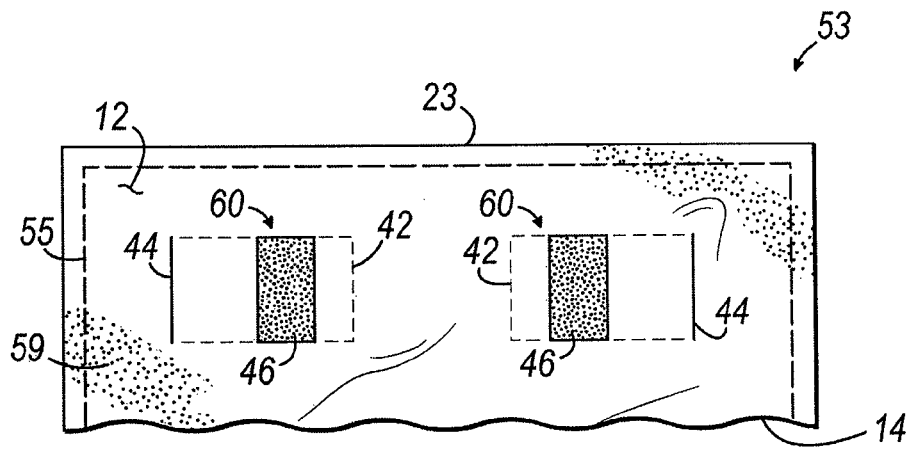
FIG. 10 is a top broken-away view showing a portion of a disposable absorbent product in accordance with another embodiment of the invention.

Variations are contemplated that may further increase the lateral extension of diaper 10. FIG. 10 illustrates an exemplary one of those variations. For ease of understanding, like reference numerals in FIG. 10 refer to similar features in the preceding figures. In that embodiment, the diaper 53 therein has a layer 55 of elastomeric material disposed between the topsheet 12 and backsheet 14, at least in the back end region 59 thereof, that strengthens the back end region 49 relative to other embodiments that include only a topsheet 12 and a backsheet 14. In the embodiment of FIG. 10, each of the fastening components 60 is formed from a cut-out portion of the back end region 59, and accordingly also contains elastomeric material, which increases the overall extensibility of the fastening components 60. As used herein, the term "elastomeric" refers to materials capable of stretching to at least about 150% of their original dimension in the direction of the applied stretching force, and which can then retract to a dimension no greater than about 120% of their original dimension, in the direction of the applied stretching force. Exemplary elastomeric materials suitable to be used with the disposable absorbent products used herein include materials described in U.S. Patent Application Publication 2006/0216473, based on U.S. patent application Ser. No. 11/388,999, and entitled "METHODS OF MANUFACTURING MULTILAYER ELASTOMERIC LAMINATES, AND LAMINATES." The entire contents of that publication are hereby expressly incorporated by reference herein.

Figure 11:
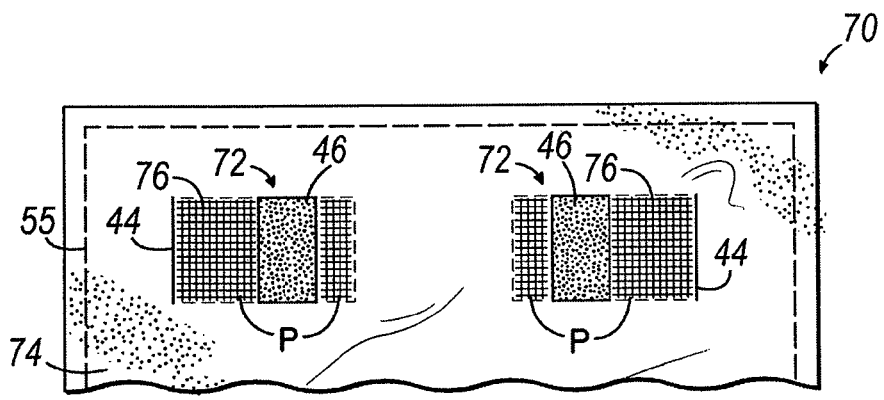
FIG. 11 is a top broken-away view showing a portion of a disposable absorbent product in accordance with yet another embodiment of the invention.

The layer 55 of elastomeric material in the fastening components 60 increases the lateral extensibility of diaper 53 to levels higher than that available with similarly sized diapers in which no elastomeric material is present. FIG. 11, in which like reference numerals refer to similar features in the preceding figures, illustrates yet another exemplary embodiment of a diaper 70, that has a level of lateral extensibility that is even higher than that available with diaper 53 (FIG. 10). In the embodiment of FIG. 11, the fastening components 72, as well as surrounding portions of the back end portion 74 of diaper 70, have a layer 55 of elastomeric material therein. Notably, in that embodiment, at least a portion, if not the entire main body 76 of each fastening component 72, is activated. For ease of illustration and understanding, the activated regions in FIG. 11 are shown as patterned areas, and designated with the letter P.

As used herein, the term "activated" and related terms refer to a process by which an elastomeric film or laminate is rendered easy to stretch. Most often, activation is a physical modification or deformation of a layer of elastomeric film. Stretching a film for the first time is one way of activating the film. An elastomeric material that has undergone activation is called "activated." A common example of activation is blowing up a balloon. The first time the balloon is blown up ("activated"), the material in the balloon is stretched. If the material in the balloon is difficult to stretch, the person inflating the balloon will often manually stretch the uninflated balloon to make the inflation easier. If the inflated balloon is allowed to deflate and then blown up again, the "activated" balloon is much easier to inflate.

In the embodiment of FIG. 11, activation of the back end portion 74 is effected such that only a main body 76 of each fastening component 72 is activated, while leaving adjacent areas of the back end portion 74 that also contain elastomeric material therein free of activation i.e., unactivated. But alternative embodiments are contemplated in which other areas of back end portion 74, adjacent fastening component 72, are also activated. An exemplary process for activating materials is provided by passing a web through a pair of intermeshing rolls, as described for example in U.S. Pat. No. 5,422,172, entitled "ELASTIC LAMINATED SHEET OF AN INCREMENTALLY STRETCHED NONWOVEN FIBROUS WEB AND ELASTOMERIC FILM AND METHOD," the entire contents of which are hereby expressly incorporated by reference herein. In that regard, a pair of pitched intermeshing rolls may be used for this targeted activation of main body 76.

Figure 12:
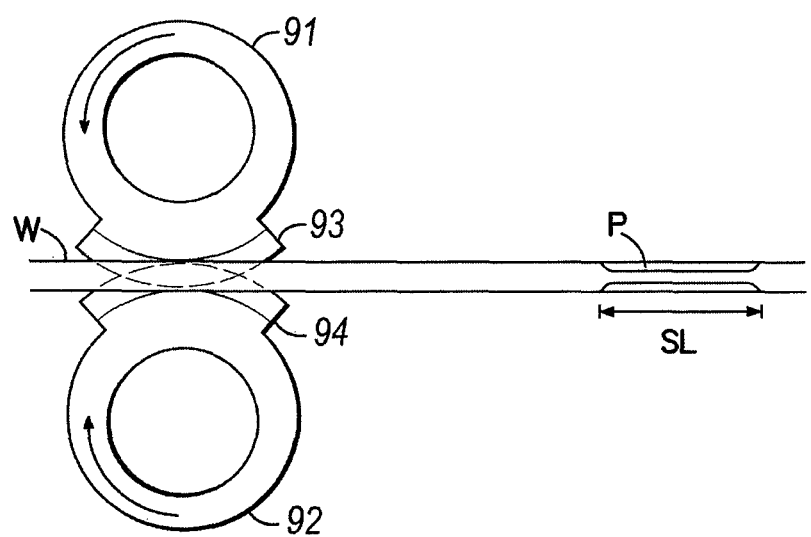
FIG. 12 is an elevation schematic view of an exemplary pair of intermeshing rolls in accordance with one embodiment of the invention.

Pitched intermeshing rolls are rolls, such as the exemplary rolls 91, 92 schematically represented in FIG. 12, that have a discontinued circumference. Passing of a web W between the rolls 91, 92 may be used to target a specific length SL of activation in web W. The resulting activated area P in the web W has a length SL corresponding to the length (along the circumference of rolls 91, 92) of the intermeshing ribbed sections 93, 94 of rolls 91, 92. The width of the activated area, on the other hand, corresponds to the width of the intermeshing ribbed sections 93, 94 (in the view of FIG. 12, the dimension normal to the plane of the paper).

While the embodiments of FIGS. 1-11 have the fastening components 40, 40a, 40b, 40c located in the back end portion 33 of diaper 10, 10a, 10b, 10c, those of ordinary skill in the art will readily appreciate that they may instead be located in other regions of the back longitudinal half 19 of diaper 10, 10a, 10b, 10c with that type of alternative embodiment still falling within the scope of the present disclosure. Further, other embodiments are contemplated in which the fastening components 40, 40a, 40b, 40c are instead located in the front end portion 31 or in other regions of the front longitudinal half 17. In those embodiments, a cooperating fastening feature such as fastening feature 50 (FIG. 1) would be located in the back longitudinal half 19 so as to cooperate with the fastening components 40, 40a, 40b, 40c (located in front longitudinal half 17) to secure the diaper 10 in place on the body of the wearer.

Referring again to FIGS. 1-6, while the fastening components 40 in the embodiment illustrated in those figures includes a solid joint 42 defining the pivotal coupling between fastening component 40 and the remainder of diaper 10, that feature is intended to be exemplary rather than limiting. Specifically, embodiments are contemplated in which the pivotal coupling between fastening component 40 and the remainder of diaper 10 is instead provided by a frangible or some other type of discontinued joint, so long as that joint is capable of maintaining the fastening component 40 joined to the remainder of diaper 10 through the first and second conditions thereof described above (FIGS. 3-6) and, generally, during use.

Yet other variations are contemplated. For example, and without limitation, the diaper 10 of FIG. 1 has both of the pairs of fastening components 38 and 40 located in the back longitudinal half 19. These fastening components 38, 40 may instead be located in the front longitudinal half 17, which may be a desirable feature for some wearers of the diaper 10. Alternatively also, embodiments are contemplated in which one of the pairs of fastening components 38, 40 is located in the front or back longitudinal half 17, 19, while the other of the pairs of fastening components 38, 40 is located in the other of the longitudinal halves 17, 19. In those embodiments, any corresponding cooperating fastening feature (e.g., fastening features 39 or 50 of FIG. 1) would be located in the longitudinal half opposite that in which its corresponding fastening component 38, 40 is located.

From the above disclosure of the general principles of the present invention and the preceding detailed description of exemplary embodiments, those skilled in the art will readily comprehend the various modifications to which this invention is susceptible. Accordingly, this invention is intended to be limited only by the scope of the following claims and equivalents thereof.

What is claimed is:

1. A disposable absorbent product extending along a longitudinal axis between front and back longitudinal ends of the disposable absorbent product, and along a transverse axis orthogonal to the longitudinal axis, the disposable absorbent product comprising:
   a topsheet defining an interior face of the disposable absorbent product configured to face a wearer thereof during use;
   a backsheet overlaying said topsheet, said backsheet defining an exterior face of the disposable absorbent product configured to face away from the wearer during use;
   an absorbent core disposed between said topsheet and said backsheet for storing fluid secreted by the wearer of the disposable absorbent product; and
   a first pair of fastening components, each being formed from a partially cut-out portion of the disposable absorbent product so as to be pivotally coupled to a remainder of the disposable absorbent product, wherein pivotal movement of said fastening components relative to a remainder of the disposable absorbent product defines at least one aperture extending between said interior and exterior faces.

2. The disposable absorbent product of claim 1, wherein pivotal movement of said fastening components relative to the remainder of the disposable absorbent product defines a pair of laterally spaced apart apertures extending between said interior and exterior faces.

3. The disposable absorbent product of claim 1, wherein
   said absorbent core has first and second longitudinal edges,
   said absorbent core is longitudinally positioned in the disposable absorbent product so as to leave first and second end portions respectively between said first longitudinal edge and one of the front or back longitudinal ends, and between said second longitudinal edge and the other of the front or back longitudinal ends,
   each of said fastening components is formed from a partially cut-out portion in said first end portion, each of said fastening components is pivotally coupled to said first end portion, and pivotal movement of each of said fastening components relative to said first end portion defines said at least one aperture, said at least one aperture being located in said first end portion.

4. The disposable absorbent product of claim 3, wherein said first longitudinal edge of said absorbent core is proximate the back longitudinal end, said first end portion extends between said first longitudinal edge and the back longitudinal end, and said fastening components are located in said first end portion.

5. The disposable absorbent product of claim 1, wherein each of said fastening components includes a mechanical fastening element.

6. The disposable absorbent product of claim 1, wherein each of said fastening components includes an interior face coplanar with said interior face of the disposable absorbent product, and an exterior face coplanar with said exterior face of the disposable absorbent product, and a fastening element coupled to said interior face of said fastening component.

7. The disposable absorbent product of claim 1, wherein at least a portion of each of said fastening components is activated.

8. The disposable absorbent product of claim 7, wherein said activated portion has a layer of elastomeric material therein.

9. The disposable absorbent product of claim 1, further comprising:

a layer of elastomeric material disposed between said topsheet and backsheet, said fastening components including said elastomeric material, wherein at least a portion of each of said fastening components containing said elastomeric material is activated.

10. The disposable absorbent product of claim 9, wherein areas of the disposable absorbent product containing said elastomeric material and adjacent said fastening components are free of activation.

11. The disposable absorbent product of claim 1, wherein the transverse axis divides the disposable absorbent product into front and back longitudinal halves, the disposable absorbent product further comprising:

a second pair of fastening components located on one of the front or back longitudinal halves and engageable with a cooperating fastening feature on the other of the first or second longitudinal halves so as to secure the disposable absorbent product in place during use.

12. The disposable absorbent product of claim 11, wherein said fastening feature is a component attached to said backsheet.

13. The disposable absorbent product of claim 11, wherein said fastening feature is defined by an exterior surface of said backsheet.

14. The disposable absorbent product of claim 1, further comprising:

a fastening feature attached to said backsheet and engageable by at least one of said fastening components to secure the disposable absorbent product in place during use.

15. The disposable absorbent product of claim 1, wherein each of said fastening components is joined to a remainder of the disposable absorbent product through a frangible joint.

16. The disposable absorbent product of claim 15, wherein each of said fastening components is further joined to the remainder of the disposable absorbent product through a solid joint.

17. A disposable absorbent product extending in a longitudinal dimension between front and back longitudinal ends thereof, and in a width dimension orthogonal to the longitudinal dimension, the disposable absorbent product comprising:

a topsheet defining an interior face of the disposable absorbent product configured to face a wearer thereof during use;

a backsheet overlaying said topsheet, said backsheet defining an exterior face of the disposable absorbent product configured to face away from the wearer during use;

an absorbent core disposed between said topsheet and said backsheet for storing fluid secreted by the wearer of the disposable absorbent product; and a pair of fastening components, each including an interior face and an exterior face disposed opposite said interior face of said fastening component, each fastening component having a first condition in which said exterior face thereof is coplanar with said exterior face of the disposable absorbent product, and a second condition in which said exterior face of said fastening component is not coplanar with said exterior face of the disposable absorbent product, movement of the fastening components between said first and second conditions defining at least one aperture adjacent at least one of said fastening components and extending between said interior and exterior faces of the disposable absorbent product.

18. The disposable absorbent product of claim 17, further comprising:

a frangible joint between each of said fastening components and a remainder of the disposable absorbent product, wherein movement of said fastening components from said first condition to said second condition includes rupturing of said frangible joint.

19. The disposable absorbent product of claim 18, further comprising:

a solid joint between each of said fastening components and said remainder of the disposable absorbent product, said solid joint coupling said fastening component to said remainder of the disposable absorbent product in said first and second conditions.

* * * * *